United States Patent [19]

Goetz

[11] 4,405,821

[45] Sep. 20, 1983

[54] PROCESS FOR PREPARING GLYCOLALDEHYDE AND/OR ETHYLENE GLYCOL

[75] Inventor: Richard W. Goetz, Cincinnati, Ohio

[73] Assignee: National Distillers and Chemical Corporation, New York, N.Y.

[21] Appl. No.: 291,749

[22] Filed: Aug. 11, 1981

[51] Int. Cl.³ .................... C07C 29/14; C07C 31/20
[52] U.S. Cl. .................................... 568/862; 568/462
[58] Field of Search ............... 568/462, 862, 884, 840

[56] References Cited

U.S. PATENT DOCUMENTS

| | | | |
|---|---|---|---|
| 2,451,333 | 10/1948 | Gresham et al. | 568/862 |
| 3,527,809 | 9/1970 | Pruett et al. | 568/454 |
| 3,544,635 | 12/1970 | Kehoe et al. | 568/909 |
| 3,557,219 | 1/1971 | Kehoe et al. | 568/909 |
| 3,833,634 | 9/1974 | Pruett et al. | 568/462 |
| 3,917,661 | 11/1975 | Pruett et al. | 568/454 |
| 3,920,753 | 11/1975 | Toshihide et al. | 568/462 |
| 3,948,964 | 4/1976 | Cawse | 568/862 |
| 4,200,765 | 4/1980 | Goetz | 568/862 |

*Primary Examiner*—Werren B. Lone
*Attorney, Agent, or Firm*—Kenneth D. Tremain

[57] ABSTRACT

In the process for producing glycolaldehyde and/or ethylene glycol by the reaction of formaldehyde, carbon monoxide and hydrogen in a non-amide solvent at elevated temperature and superatmospheric pressure in the presence of a catalytic amount of a rhodium-containing catalyst, an improvement is provided which comprises carrying out said reaction in the presence of a glycolaldehyde yield-enhancing phosphine oxide.

21 Claims, No Drawings

PROCESS FOR PREPARING GLYCOLALDEHYDE AND/OR ETHYLENE GLYCOL

BACKGROUND OF THE INVENTION

This invention is concerned with processes for the preparation of glycolaldehyde, and conversion thereof to ethylene glycol, by reaction of formaldehyde, carbon monoxide and hydrogen in the presence of a rhodium catalyst.

Ethylene glycol is a very valuable commercial chemical with a wide variety of uses including use as a coolant and anti-freeze, monomer for polyester production, solvent, and an intermediate for production of commercial chemicals.

Glycolaldehyde is a valuable intermediate in organic synthesis, including the preparation of serine, and is particularly useful as an intermediate in the production of ethylene glycol by catalytic hydrogenation.

The reaction of formaldehyde with carbon monoxide and hydrogen is a known reaction and yields, inter alia, ethylene glycol, methanol, and higher polyhydroxy compounds. For example, U.S. Pat. No. 2,451,333 describes the reaction of formaldehyde, carbon monoxide and hydrogen over a cobalt catalyst to produce mixtures of polyhydroxy compounds which include ethylene glycol, glycerol, and higher polyols. Various metal catalysts are also disclosed including nickel, manganese, iron, chromium, copper, platinum, molybdenum, palladium, zinc, cadmium, ruthenium and compounds thereof.

U.S. Pat. No. 3,920,753 describes the production of glycolaldehyde by reaction of formaldehyde with carbon monoxide and hydrogen in the presence of a cobalt catalyst under controlled reaction conditions, but with comparatively low yields.

Polyols are also produced by reaction of carbon monoxide and hydrogen over various metal catalysts. U.S. Pat. No. 3,833,634 describes this reaction catalyzed by rhodium to produce ethylene glycol, propylene glycol, glycerol, methanol, ethanol, methyl acetate, etc. Rhodium catalysts are also employed in the production of oxygenated derivatives of alkenes, alkadienes and alkenoic acid ester by reaction with carbon monoxide and hydrogen, as described, for example, in U.S. Pat. Nos. 3,081,357; 3,527,809; 3,544,635; 3,557,219; and 3,917,661.

The prior art processes for production of ethylene glycol have characteristically provided mixtures of products, the principal co-products being propylene glycol and glycerine, along with the lower alcohols, methyl and ethyl alcohol. Thus, these processes are encumbered by the need for expensive and time-consuming separation techniques where ethylene glycol is the desired product. In addition, the efficiency of the reaction in terms of yield of ethylene glycol is not high due to the concomitant formation of the co-products, which are usually present in significant amounts.

In accordance with U.S. Pat. No. 4,200,765 which is incorporated by reference herein, the reaction of formaldehyde, carbon monoxide and hydrogen over a rhodium-containing catalyst appears to involve a two-stage reaction, with the first stage yielding glycolaldehyde and methanol, and the second stage yielding ethylene glycol. Thus, this reaction is analogous to that realized with cobalt catalysts as collectively disclosed in the aforementioned U.S. Pat. Nos. 2,451,333 and 3,920,753, the surprising difference residing in the high selectivity of the process of U.S. Pat. No. 4,200,765 which exclusively leads to ethylene glycol as the sole detectable polyol obtained in the second stage of the reaction. Further, the conversion to glycolaldehyde realized in the first stage of the process of U.S. Pat. No. 4,200,765 is substantially greater than that obtained in the process described in U.S. Pat. No. 3,920,753.

When, in accordance with the preferred procedure, The process of U.S. Pat. No. 4,200,765 is carried out employing an aprotic amide solvent such as 1-methylpyrrolidin-2-one, 1-ethylpyrrolidin-2-one, 1-benzylpyrrolidin-2-one and N,N-diethylacetamide, the first stage conversion to glycolaldehyde proceeds very well with good yields and high formaldehyde conversion rates. However, in non-amide solvents, either of the protic or the preferred aprotic variety, yields of glycolaldehyde have been found to be comparatively poor.

SUMMARY OF THE INVENTION

It has now been discovered that when formaldehyde, carbon monoxide and hydrogen are reacted in a first stage in a non-amide solvent at elevated temperature and pressure in the presence of a rhodium-containing catalyst composition to provide glycolaldehyde as described in U.S. Pat. No. 4,200,765, the yield of glycolaldehyde can be substantially improved when a phosphine oxide is present in the reaction medium. Methanol is a by-product of the foregoing reaction.

The product glycolaldehyde readily tends to form acetals, a reaction typical of aldehydes, and in view of the primary alcohol group present in the molecule, this compound forms hemi-acetals and acetals with itself in the form of, for example, linear and cyclic acetals, represented by the formulas:

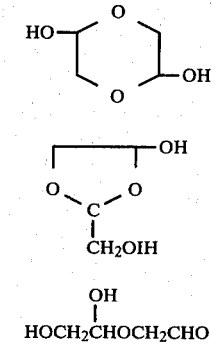

Glycolaldehyde may also form acetals and hemiacetals with methanol, and, if present, ethylene glycol. If desired, glycolaldehyde can be recovered from the reaction medium as an acetal and/or hemiacetal with the free aldehyde later being obtained by hydrolysis. In the form of its dimer(s), glycolaldehyde is a useful intermediate in the production of 1,1,2-triacetoxyethane, the latter itself being a useful intermediate for the production of d,l-serine, a feed supplement widely used in the poultry industry.

Alternatively, the glycolaldehyde can be chemically reduced without prior separation from the medium in which it is produced in a second stage reaction to provide ethylene glycol as hereinafter more fully described.

DESCRIPTION OF THE PREFERRED EMBODIMENTS

In accordance with the first stage reaction of the present process, formaldehyde, carbon monoxide and hydrogen are reacted in a non-amide solvent at superatmospheric pressure and temperature in the presence of a rhodium-containing catalyst composition and a phosphine oxide.

The catalyst for the first stage reaction can be elemental rhodium, or a rhodium compound, complex or salt, or mixtures thereof, employed as such or deposited or affixed to a solid support such as molecular sieve zeolites, alumina, silica, anion exchange resin or a polymeric ligand. In the active form, the catalyst comprises rhodium in complex combination with carbon monoxide, i.e., rhodium carbonyl, which may contain additional ligands as described, for example, in U.S. Pat. No. 3,527,809 and the aforementioned U.S. Pat. No. 3,833,634, each of which is incorporated herein by reference for the disclosure of rhodium complexes containing carbon monoxide and organic ligands as well as hydrogen as a ligand. As described in U.S. Pat. No. 3,833,634, suitable organic ligands are compounds which contain at least one nitrogen and/or at least one oxygen atom, said atoms having a pair of electrons available for formation of coordinate bonds with rhodium. Illustrative organic ligands include various piperazines, dipyridyls, N-substituted diamines, aminopyridines, glycolic acid, alkoxy-substituted acetic acids; tetrahydrofuran, dioxane, 1,2-dimethoxybenzene, alkyl ethers of alkylene glycols, alkanolamines, iminodiacetic acid, nitrilotriacetic acid, ethylenediaminetetraacetic acid, and the like. In U.S. Pat. No. 3,527,809 are described phosphorus-containing ligands such as trialkyl, triaryl and tricycloalkyl phosphites and triarylphosphines, as well as the analogous antimony and arsenic compounds.

Especially preferred catalysts are those including phosphines as ligand, particularly triarylphosphines, such as triphenylphosphine. Illustrative catalysts are wellknown and described in the scientific literature. Most preferred of such catalysts are those which include halide, preferably chloride, which result in higher yield of glycolaldehyde in shorter reaction times than corresponding nonchloride-containing catalysts.

The phosphine-containing catalysts can be prepared by the methods described in the aforesaid U.S. Pat. No. 3,527,809 employing suitable ligands exemplified as follows:

| | |
|---|---|
| Trimethylphosphine | Ethyl-bis(beta-phenylethyl)phosphine |
| Triethylphosphine | Tricyclopentylphosphine |
| Tri-n-butylphosphine | Tricyclohexylphosphine |
| Triamylphosphines | Dimethylcyclopentylphosphine |
| Trihexylphosphines | Trioctylphosphine |
| Tripropylphosphine | Dicyclohexylmethylphosphine |
| Trinonylphosphines | Phenyldiethylphosphine |
| Tridecylphosphines | Dicyclohexylphenylphosphine |
| Triethylhexylphosphine | Diphenylmethylphosphine |
| Di-n-butyloctadecylphosphine | Diphenylbutylphosphine |
| Dimethylethylphosphine | Diphenylbenzylphosphine |
| Diamylethylphosphine | Trilaurylphosphine |
| Tris(dimethylphenyl)phosphine | Triphenylphosphine |

Using this procedure, preferred catalysts can be prepared by selection of suitable ligands and rhodium compounds, including the following:

$RhCl(CO)(PPh_3)_2$
$RhCl(PPh_3)_3$
$RhBr(CO)(PPh_3)_2$
$RhI(CO)(PPh_3)_2$
$RhCl(CO)(PEt_3)_2$
$RhCl(CO)[P(p-MeC_6H_4)_3]_2$
$RhCl(CO)[P(p-MeOC_6H_4)_3]_2$
$RhCl(CO)[P(p-FC_6H_4)_3]_2$
$RhCl_3(CO)(PPh_3)_2$
$RhCl_3(PEt_2Ph)_3$
$Rh(CO)H(PPh_3)_3$
$RhCl(CO)(PEt_2Ph)_2$

The catalyst can be employed in soluble form or in suspension in the reaction medium, or alternatively deposited on porous supports. The catalyst can be prepared by various techniques. For example, the complex with carbon monoxide can be preformed and then introduced into the reaction medium, or, alternatively, the catalyst can be formed in situ by reaction of rhodium, or rhodium compound, directly with carbon monoxide which may be effected in the presence of a selected organic ligand to form the organic ligand-carbon monoxide-rhodium complexes in the reaction medium.

The amount of catalyst employed in the first stage reaction does not seem to be critical and can vary considerably. At least a catalytically effective amount of catalyst should be used, of course. In general, an amount of catalyst which is effective to provide a reasonable reaction rate is sufficient. As little as 0.001 gram atoms of rhodium per liter of reaction medium can suffice while amounts in excess of 0.1 gram atoms do not appear to materially affect the rate of reaction. For most purposes, the effective preferred amount of catalyst is in the range of from about 0.002 to about 0.025 gram atoms per liter.

The phosphine oxide compounds suitable for the practice of the process of the present invention are those which include a single phosphoryl group, and the remaining atoms bonded to the phosphorus are carbon which may be substituted by at least another carbon atom, hydrogen, fluorine and/or oxygen. The phosphine oxide compounds should be free of sulfur atoms and halogen atoms except fluorine. Phosphine oxides of this type and as such, useful in the practice of this invention, are disclosed in U.S. Pat. No. 4,197,253 which is incorporated by reference herein. Preferred phosphine oxides include:

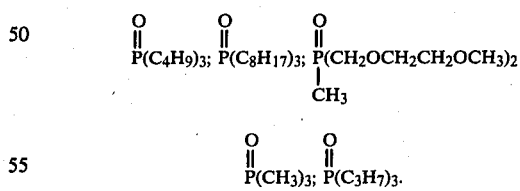

These and other useful phosphine oxides can be prepared in accordance with known methods such as those set forth in G. M. Kosolapoff, et al., "Organic Phosphorus Compounds," Volume 3, John Wiley & Sons, Inc. 1972, pp. 341–500 which is incorporated by reference herein. The phosphine oxides can be used in widely varying amounts with amounts of from about 0.5 to about 50 weight percent of the mixture exclusive of reaction product(s), and preferably from about 0.5 to about 30 weight percent, and most preferably from about 5 to about 25 weight percent, generally providing good results.

The manner of contact of the formaldehyde, carbon monoxide and hydrogen reactants is not critical since any of the various procedures normally employed in this type of reaction can be used as long as efficient gas-liquid contact is provided. Thus, the process can be carried out by contacting a solution of formaldehyde together with the rhodium catalyst with a mixture of carbon monoxide and hydrogen at the selected conditions. Alternatively, the solution of formaldehyde can be passed over the catalyst in a trickle phase under a mixture of carbon monoxide and hydrogen at the selected conditions of temperature and pressure. As with any process of this kind, the present process can be conducted in batch, semi-continuous, and continuous operation. The reactor should be constructed of materials which will withstand the temperatures and pressures required, and the internal surfaces of the reactor are substantially inert. The usual controls can be provided to permit control of the reaction such as heat-exchangers and the like. The reactor should be provided with adequate means for agitating the reaction mixture; mixing can be induced by vibration, shaking, stirring, oscillation and like methods. Catalyst as well as reactants may be introduced by vibration, shaking, stirring, oscillation and like methods. Catalyst as well as reactants may be introduced into the first stage or the second stage reactor at any time during the process for replenishment. Recovered catalyst, solvent and unreacted starting materials may be recycled.

The reaction is carried out in a non-amide (preferably aprotic) solvent. Suitable solvents include nitriles, such as acetonitrile, benzonitrile, propionitrile and the like; cyclic ethers such as tetrahydrofuran, dioxane and tetrahydropyran; acyclic ethers such as diethyl ether, 1,2-dimethoxybenzene, alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; esters, such as ethyl acetate, ethyl propionate and methyl laurate; lactones of organic carboxylic acids such as butyrolactone and valerolactone; organic acids such as acetic acid, propionic acid and caproic acid; and alkanols, such as methanol, ethanol, propanol, 2-ethylhexanol and the like; and mixtures thereof. Many of the solvents are non-reactive in the medium whereas others are capable of functioning as ligands. The selected solvent should preferably be liquid under the reaction conditions.

The first stage reaction is generally carried out at a temperature of at least about 100° C. to obtain a reasonable reaction rate although somewhat lower temperatures can be employed with slower reaction rates being realized. For reaction times of about one hour, and even less, the temperature should be in the range of from about 100° C. to about 175° C., preferably from about 120° to about 160° C. The partial pressure of carbon monoxide is preferably high in comparison to that of hydrogen, with the preferred ratios being from about 3:1 to about 1:3, the more preferred being from about 3:2 to about 2:3. The total pressure of gas used is generally maintained at from about 1,000 psi up to about 9,000 psi, with from about 3,000 to about 7,000 psi being preferred. Of course, higher pressures and higher temperatures can be used but with no appreciable advantage and, since they require the use of special high pressure equipment, they are usually avoided.

The source of formaldehyde for the present process can be any of those commonly used in this technology including paraformaldehyde, methylal, formalin solutions, and polyoxymethylenes. Of these, paraformaldehyde is preferred since best yields are attained therewith. Solutions of formaldehyde in solvents, advantageously the reaction solvent, can be used.

The reaction pressures represent the total pressure of the gases contained in the reactor, i.e., carbon monoxide and $H_2$, and, if present, any inert diluent gas such as nitrogen. As in any gaseous system, the total pressure is the sum of partial pressures of component gases. In the present reaction, the molar ratio of hydrogen to carbon monoxide can range from about 1/10 to about 10/1, with the preferred ratio, from about 1/5 to about 5/1, and the reaction pressure can be achieved by adjusting the pressure of these gases in the reactor.

For best results, an approximately equimolar ratio of carbon monoxide and hydrogen is maintained in the first stage reaction to favor production of glycolaldehyde. In the second stage reaction, high partial pressure of hydrogen is desirable for the reduction reaction. Thus, in the first stage reaction to produce glycolaldehyde, the partial pressure of carbon monoxide is usually adjusted to be about 3 to about 10 times that of hydrogen. In the second stage reaction, the partial pressure of hydrogen is adjusted to a high value to facilitate the reaction. Such adjustments of the gas feed can be readily accomplished. For example, after the first phase reaction is substantially complete, the reactor need only be bled to lower the pressure and then pressurized with hydrogen gas to achieve the desired high partial pressure of hydrogen. Carbon monoxide present in the gaseous system of the first phase reaction need not be completely purged from the reactor prior to repressurizing with hydrogen gas. Of course, carbon monoxide can reduce the efficiency of certain catalyst systems, possibly through poisoning as is known, and preferably is excluded when such systems are employed.

When glycolaldehyde is the desired product, of course, only the first stage reaction need be carried out. The product obtained is usually in the form of the aforementioned acetals and/or hemiacetals and can be separated from the coproduced methanol and reaction solvent, if necessary, by fractional distillation. Gas chromatography and mass spectrophotometric analysis are used to identify the product as glycolaldehyde. In addition, the dimedone (5,5-dimethylcyclohexane-1,3-dione) derivative of pure glycolaldehyde was prepared and compared with the dimedone derivative of the product obtained from the typical reaction according to the present process to show them to be identical. NMR analysis of the derivative confirmed glycolaldehyde as the product. No glyoxal was detected by any of the aforementioned analytical techniques.

In the first stage reaction which results in glycolaldehyde and methanol, production is usually substantially complete in relatively short reaction times, usually less than about one hour, with substantial yield of product realized in as little as 30 minutes, and even less time. Usually, only small amounts of ethylene glycol, if any, can be detected.

When it is desired to combine the first stage production of glycolaldehyde with a second stage whereby the glycolaldehyde is chemically reduced to ethylene glycol, implementation of the two-stage process can take several forms. The reaction can be accomplished by allowing both stages to proceed consecutively at suitable temperature and pressure, or alternatively the reaction can be stopped at the end of the first stage where the product is glycolaldehyde and the second stage can be carried out under any applicable reduction process which will result in conversion of the aldehyde group of glycolaldehyde to a primary alcohol group resulting in ethylene glycol.

A wide variety of reduction processes can be employed for the second stage reaction including the well-known chemical reducing agents employed in reducing aldehydes to primary alcohols. For commercial processes, however, where possible, catalytic reductions employing hydrogen are usually preferred since they are more practical and efficient especially with catalysts which can be regenerated and thus are re-usable. In the present process, catalytic hydrogenation is preferred for these same reasons, especially with catalysts which can be regenerated. Any hydrogenation catalyst can be employed.

Thus, typical hydrogenation catalysts include, for example, Raney Nickel, cobalt, copper chromite, rhodium, palladium, platinum, and similar such metal catalysts, which can be used conveniently on supports such as charcoal, silica, alumina, kieselguhr and the like. The conditions of catalytic hydrogenations are well-known and, in general, the reaction can be conducted at temperatures ranging from about 30° to about 150° C., usually at pressures of from about 100 to about 5000 psig. The use of higher temperatures and pressures, though operable, provides no special advantage and usually requires special equipment which economically is disadvantageous and therefore not preferred.

Particularly preferred catalysts are those which characteristically require short reaction times, e.g., palladium and nickel, which is most desirable for commercial processes for economic reasons.

When the glycolaldehyde is present in the form of an acetal and/or hemiacetal, the latter is preferably hydrolyzed to the free aldehyde so that efficient reduction to ethylene glycol can be effected.

The hydrolysis reaction can be accomplished merely by assuring the presence of water in the reaction mixture, preferably in at least equivalent molar quantities. Thus, equimolar amounts of water are required to assure complete hydrolysis, with less than equimolar amounts resulting in less than complete hydrolysis of the acetal present in the mixture which, in turn, results in lower yield of ethylene glycol. It is convenient to hydrolyze the acetal immediately prior to and/or concurrently with the reduction stage.

Oftentimes, the amount of water required for substantial hydrolysis of the aforementioned acetals may already be present in the first stage reaction which ideally contains small amounts of water for best results, e.g., from about 0.5 to about 10% by volume. Alternatively, where insufficient water is present, the necessary water level can be achieved by mere addition of water to the second stage reaction, either batchwise or by metering over the course of the reaction. In experience to the present time, optimum final levels of water are in the range of from about 10-30% by volume based on the hydrogenation mixture.

To facilitate hydrolysis, the presence of an acid is particularly desirable. Thus, strong mineral acids, such as hydrohalic acids, sulfuric, and phosphoric acids or, preferably, weak organic acids, especially lower alkanoic acids such as acetic and propionic acids, can be employed for this purpose. The amount of acid employed does not appear to be critical and even trace amounts are effective, as should be obvious to those skilled in this art.

Thus, it is apparent that a separate hydrolysis step is not always necessary since the normal water content of the first stage reaction will hydrolyze at least part of the acetals produced and the hydrolyzed part will reduce to ethylene glycol. However, maximizing yield of ethylene glycol dictates the inclusion of a hydrolysis step to assure maximum hydrolysis and thus the highest realizable yield of ethylene glycol. Accordingly, the inclusion of the hydrolysis step, though not always essential, amounts to good technique, which, in view of the simplicity of adding water, with or without acid present, is readily practicable.

The combined hydrolysis-hydrogenation step can be carried out by art-recognized techniques as described, for example, in U.S. Pat. Nos. 4,024,197; 2,721,223; 2,888,492 and 2,729,650 incorporated herein by reference for the disclosed combined reactions.

As should be apparent, the rhodium catalyst employed in the first stage reaction can also serve as the hydrogenation catalyst for the second stage reaction to produce ethylene glycol. Thus, if the first phase reaction is allowed to continue, eventually the hydrogenation reaction will yield ethylene glycol. Particularly excellent yields are obtained by adding water, where necessary, to hydrolyze the glycolaldehyde acetals present from the first stage reaction thus realizing maximum yields of ethylene glycol. In general, the rhodium catalyst of the first stage reaction is an effective catalyst for the second stage hydrogenation, but does not provide as short reaction times as can be realized with other hydrogenation catalysts, under the usual reaction conditions.

To shorten the second stage reaction time, it is possible to effect the reduction step over metal catalysts such as palladium and nickel, and it is usually preferred to effect the second stage reaction in a separate reactor. Thus, the first stage reaction can be conducted in a first reactor under selected conditions of temperature and pressure, and after completion the first stage product, with or without isolation from the reaction mixture, can then be transferred to a second reactor under selected conditions of temperature and pressure to effect the hydrogenation reaction under hydrolysis conditions, i.e., in the presence of at least the stoichiometric amount of water to hydrolyze the glycolaldehyde acetals present.

Alternatively, the two stage reaction can be conducted in one reactor with provision for controlling the reaction parameters. At the time of the hydrogenation stage, the selected hydrogenation catalyst can be added, conveniently with the water required for hydrolysis, if any is needed, and the hydrogenation reaction can then proceed. In this latter modification, the hydrogenation catalyst can be added to the first phase reaction mixture with or without the first phase rhodium catalyst being present. Generally, it is preferred to remove the rhodium catalyst, particularly if this can be done conveniently so that competitive catalysis will not impede the hydrogenation reaction, and, more importantly, to permit more accurate control over the reaction.

Where the second phase reaction is carried out in a separate reactor, whether over the originally present rhodium catalyst or a different metal hydrogenation catalyst, the reaction is normally conducted under hydrogen gas without diluent gas, as is usual in catalyzed hydrogenation reactions.

The present invention, therefor, provides a simplified process for selective production of glycolaldehyde as the sole detectable aldehyde product. In addition, this invention affords a simplified process for obtaining ethylene glycol by either allowing the initial process for glycolaldehyde to continue so that hydrogenation under hydrolytic conditions yields ethylene glycol or, alternatively, the glycolaldehyde product of the first stage reaction is reduced under hydrolytic conditions employing art-recognized reduction processes to ethylene glycol. In the latter process, the glycolaldehyde product of the first stage reaction can be used in the form of the reaction mixture, or the product can be isolated, as by fractionation, and used in purified form.

The following examples further illustrate the invention:

EXAMPLES 1-7

These examples illustrate the improved results obtained when the phosphine oxide, tributylphosphine oxide, is present in the reaction medium. The amounts of each component of the reaction medium (charged to a 70 ml pressure reactor) and the conditions under which each reaction was carried out were as follows:

| Component | Amount |
|---|---|
| $RhCl(PPhenyl_3)$ | 0.038 g |
| 97% Paraformaldehyde | 0.61 g |
| Tributylphosphine oxide | 1.5 g (except Example 4 in which 2.5 g where added) |
| Water | 0.4 ml |
| Solvent | 7.2 ml |
| $H_2$:CO ratio | 1 |

The $H_2$/CO mixture was charged to the reactor at 3550 psig and the reactor was heated to 140° C. After 30 minutes, the percent yield of glycolaldehyde for each run was determined. The results are set forth in Table I as follows:

TABLE I

| | | % Glycolaldehyde Yield | |
|---|---|---|---|
| Example | Solvent | With Tributyl-phosphine Oxide | Without Tributyl-phosphine Oxide |
| 1 | Benzonitrile | 53 | 4 |
| 2 | Ethylene diacetate | 59 | 0 |
| 3 | Tetraglyme | 51 | 5 |
| 4 | Gamma-Butyrolactone | 63 | 17 |
| 5 | Ethyl Benzoate | 35 | 5 |
| 6 | N—Benzypyrrolidone | 48 | 42 |
| 7 | Benzyl ether | 34 | 0 |

As these data show, when the process of this invention is carried out in a non-amide solvent, a dramatic increase in the yield of glycolaldehyde occurs when a phosphine oxide is present in the reaction medium as compared with the yield of glycolaldehyde resulting from substantially the same process but one in which a phosphine oxide is omitted.

EXAMPLES 8-28

The reaction medium and operating conditions employed in each of these examples was identical to that of Examples 1-7 except for the amounts of tributylphosphine oxide which are indicated in Table II. An amount of solvent was used to provide 10 ml total reaction medium. The results of these runs were as follows:

TABLE II

| Example | Solvent | Tributyl-phosphine Oxide (g) | Glycol-aldehyde % Yield | Formaldehyde % Conversion |
|---|---|---|---|---|
| 8 (Control) | N—Methyl pyrrolidone | 0 | 67 | )) |
| 9 | Acetonitrile | 1.5 | 78 | 97 |
| 10 | Gamma-Nonalactone | 2.5 | 64 | 98 |
| 11 | Gamma-Butyrolactone | 2.5 | 63 | 97 |
| 12 | Acetone | 1.5 | 62 | 97 |
| 13 | Ethylene diacetate | 1.5 | 59 | 85 |
| 14 | Benzonitrile | 1.5 | 53 | — |
| 15 | 1,4-Dioxane | 2.5 | 53 | 88 |
| 16 | Tetraglyme | 2.5 | 51 | 99 |
| 17 | Tetrahydrofuran | 2.5 | 47 | 99 |
| 18 | 1,3-Dicyanobutane | 2.5 | 42 | 80 |
| 19 | Triglyme | 2.5 | 40 | 99 |
| 20 | Toluene | 2.5 | 40 | 64 |
| 21 | Cyclohexane | 1.5 | 30 | 88 |
| 22 | 1,2,4-Trichlorobenzene | 1.5 | 29 | — |
| 23 | Water | 1.5 | 27 | 73 |
| 24 | Methylene chloride | 1.5 | 24 | 85 |
| 25 | 2-Propanol | 1.5 | 9 | 38 |
| 26 | Ethylene glycol | 2.5 | 3 | 30 |
| 27 | Methanol | 2.5 | 1 | 40 |
| 28 | 65 Wt. % Acetonitrile/ 35 Wt. % Water | 1.5 | 13 | 90 |

EXAMPLES 29-44

These examples illustrate the results obtained with a variety of catalyst systems, including several (Examples 41-44) which are outside the scope of this invention but which are given for the purpose of comparison. The equivalent concentration of metal atoms in each of the examples was 0.004 gm atom/liter. The conditions of each run were substantially the same as those employed in Examples 8-28. The results were as follows:

TABLE III

| Example | Catalyst | Tributyl-phosphine Oxide gm/10 ml | Solvent | Glycol-aldehyde % Yield | Formaldehyde % Conversion |
|---|---|---|---|---|---|
| 29 | $RhCl(PPhenyl_3)_2(CO)$ | 2.5 | Dioxane | 58 | 94 |
| 30 | $RhBr(PPhenyl_3)_3$ | 2.5 | Tetraglyme | 54 | 97 |
| 31 | $RhCl(PPhenyl_3)_3$ | 2.5 | Dioxane | 53 | 88 |
| 32 | $PhCl(PPhenyl_3)_3$ | 2.5 | Tetraglyme | 51 | 99 |
| 33 | $RhCl(PPhenyl_3)_3$ | 2.5 | Methanol | 1 | 24 |
| 34 | $Rh(CO)_2$ Acetate | 1.5 | Tetraglyme | 53 | 70 |
| 35 | $Rh(CO)_2$ Acetate | 1.5 | Acetone | 37 | 79 |
| 36 | $[Rh(CO)_2Cl]_2$ | 2.5 | Tetraglyme/trace of Acetaldehyde | 31 | 62 |

TABLE III-continued

| Example | Catalyst | Tributyl-phosphine Oxide gm/10 ml | Solvent | Glycol-aldehyde % Yield | Formaldehyde % Conversion |
|---|---|---|---|---|---|
| 37 | $RhCl_3.3H_2O$ | 2.5 | Tetraglyme | 22 | 68 |
| 38 | $RhCl_3.3H_2O$ | 2.5 | Methanol | 1 | 40 |
| 39 | $Rh_2O_3.5H_2O$ | 1.5 | Methanol | 8 | 15 |
| 40 | $Rh_2O_3.5H_2O$ | 0 | Methanol | 7 | 10 |
| 41 | $Ru_3(CO)_{12}$ | 1.5 | Tetraglyme | 2 | 15 |
| 42 | $Ru_3(CO)_{12}$ | 1.5 | Acetone | 0 | 0 |
| 43 | $Co_2(CO)_8$ | 1.5 | Acetone | 1 | 17 |
| 44 | $Co_2(CO)_8$ | 1.5 | Tetraglyme | 0 | 0 |

These data show that with few exceptions, the rhodium-containing catalysts of this invention far outperformed other catalyst systems for the production of glycolaldehyde.

EXAMPLES 45-52

These examples demonstrate the far superior results usually obtained with the use of a phosphine oxide in the reaction medium as compared with some other oxides. Tetraglyme was employed as the solvent (except in Examples 50 and 51 in which dioxane was the solvent and Example 52 in which ethylene diacetate was used) and the conditions were substantially the same as those of Examples 8-28. The results were as follows:

TABLE IV

| Example | Oxide (gm/10 ml) | Glycolaldehyde % Yield |
|---|---|---|
| 45 | Tributylphosphine oxide (1.5) | 57 |
| 46 | Tributylamine oxide (1.4) | 39 |
| 47 | Trimethylamine oxide (0.6) | 10 |
| 48 | Triphenylarsine oxide (1.5) | 6 |
| 49 | Triphenylstibine oxide (1.3) | 0 (formed benzaldehyde) |
| 50 | Triphenylphosphine oxide (3.2) | 11 |
| 51 | Trioctylphosphine oxide (4.4) | 38 |
| 52 | Trimethylamine Oxide (1.5) | 2 |

What is claimed is:

1. In a process in which formaldehyde, carbon monoxide and hydrogen are reacted in a first stage reaction in a non-amide solvent at elevated temperature and superatmospheric pressure in the presence of a catalytic amount of a rhodium-containing catalyst to provide glycolaldehyde, and the glycolaldehyde is subsequently catalytically reduced in a second stage reaction to provide ethylene glycol, the improvement which comprises carrying out said first stage reaction in the presence of a glycolaldehyde yield-enhancing phosphine oxide.

2. A process according to claim 1 wherein the phosphine oxide is tributylphosphine oxide.

3. A process according to claim 1 wherein said rhodium-containing catalyst is present during said second reaction stage.

4. A process according to claim 1 wherein a hydrogenation catalyst is present during said second stage reaction.

5. A process according to claim 4 wherein said rhodium-containing catalyst is removed from the first reaction stage product prior to said second stage reaction.

6. A process according to claim 4 wherein said hydrogenation catalyst comprises palladium.

7. A process according to claim 1 wherein the first stage reaction is carried out at a temperature of at least about 100° C.

8. A process according to claim 1 wherein the first stage reaction is carried out at a total gas pressure of about 1,000 psi to about 9,000 psi.

9. A process according to claim 1 wherein the phosphine oxide is present in an amount of from about 0.5 to about 50 weight percent of the reaction mixture exclusive of reaction product(s).

10. A process according to claim 1 wherein the non-amide solvent is a nitrile, cyclic ether, acyclic ether, alkyl ether of alkylene glycol, ketone, ester and/or lactone.

11. A process according to claim 1 wherein the formaldehyde is present in the reaction medium as paraformaldehyde.

12. A process according to claim 1 wherein the rhodium-containing catalyst contains rhodium in complex combination with carbon monoxide.

13. In the process for producing glycolaldehyde and/or ethylene glycol by the reaction of formaldehyde, carbon monoxide and hydrogen in a non-amide solvent at elevated temperature and superatmospheric pressure in the presence of a catalytic amount of a rhodium-containing catalyst, the improvement which comprises carrying out said reaction in the presence of a glycolaldehyde yield-enhancing phosphine oxide.

14. A process according to claim 13 carried out at a temperature of from about 75° C. to about 250° C. and a pressure of from about 10 to about 700 atmospheres.

15. A process according to claim 13 wherein the rhodium-containing catalyst contains rhodium in complex combination with carbon monoxide.

16. A process according to claim 13 wherein said catalyst further comprises a triorganophosphine ligand.

17. A process according to claim 13 wherein said catalyst further comprises a triarylphosphine ligand.

18. A process according to claim 13 wherein said temperature is in the range of from about 100° to about 175° C. and said pressure is in the range of from about 150 to about 400 atmospheres.

19. A process according to claim 18 wherein the molar ratio of hydrogen to carbon monoxide is from about 1/10 to about 10/1.

20. A process according to claim 13 wherein the non-amide solvent is a nitrile, cyclic ether, acyclic ether, alkyl ether of alkyl glycol, ketone, ester and/or lactone.

21. In the process for producing ethylene glycol by (a) the reaction of formaldehyde, carbon monoxide and hydrogen in a non-amide solvent at elevated temperature and superatmospheric pressure in the presence of a catalytic amount of a rhodium-containing catalyst to provide glycolaldehyde and (b) the catalytic hydrogenation of said glycolaldehyde to provide ethylene glycol, the improvement which comprises carrying out reaction (a) in the presence of a glycolaldehyde yield-enhancing phosphine oxide.

* * * * *